(12) United States Patent
Song

(10) Patent No.: US 8,455,185 B2
(45) Date of Patent: *Jun. 4, 2013

(54) ENZYMATIC DETECTION TECHNIQUES

(75) Inventor: Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/020,201

(22) Filed: Feb. 3, 2011

(65) Prior Publication Data

US 2011/0129823 A1 Jun. 2, 2011

Related U.S. Application Data

(62) Division of application No. 10/882,108, filed on Jun. 30, 2004, now Pat. No. 7,906,276.

(51) Int. Cl.
*C12Q 1/00* (2006.01)

(52) U.S. Cl.
USPC ............... 435/4; 435/7.1; 435/7.4; 435/7.72; 435/18; 435/23; 435/24; 435/287.7

(58) Field of Classification Search
None
See application file for complete search history.

(56) References Cited

U.S. PATENT DOCUMENTS

| | | |
|---|---|---|
| 4,275,149 A | 6/1981 | Litman et al. |
| 4,477,635 A | 10/1984 | Mitra |
| 4,614,723 A | 9/1986 | Schmidt et al. |
| 4,748,116 A | 5/1988 | Simonsson et al. |
| 4,962,024 A | 10/1990 | Schulte |
| 5,075,077 A | 12/1991 | Durley, III et al. |
| 5,124,254 A | 6/1992 | Hewlins et al. |
| 5,200,084 A | 4/1993 | Liberti et al. |
| 5,252,459 A | 10/1993 | Tarcha et al. |
| 5,292,652 A | 3/1994 | Dovey et al. |
| 5,464,739 A | 11/1995 | Johnson et al. |
| 5,464,741 A | 11/1995 | Hendrix |
| 5,466,574 A | 11/1995 | Liberti et al. |
| 5,514,785 A | 5/1996 | Van Ness et al. |
| 5,518,883 A | 5/1996 | Soini |
| 5,573,909 A | 11/1996 | Singer et al. |
| 5,585,273 A | 12/1996 | Lawrence et al. |
| 5,585,279 A | 12/1996 | Davidson |
| 5,591,581 A | 1/1997 | Massey et al. |
| 5,637,509 A | 6/1997 | Hemmilä et al. |
| 5,647,994 A | 7/1997 | Tuunanen et al. |
| 5,648,274 A | 7/1997 | Chandler |
| 5,670,381 A | 9/1997 | Jou et al. |
| 5,700,636 A | 12/1997 | Sheiness et al. |
| 5,731,147 A | 3/1998 | Bard et al. |
| 5,786,137 A | 7/1998 | Diamond et al. |
| 5,795,470 A | 8/1998 | Wang et al. |
| 5,837,429 A | 11/1998 | Nohr et al. |
| 5,872,261 A | 2/1999 | Bremmer et al. |
| 5,876,944 A | 3/1999 | Kuo |
| 5,922,537 A | 7/1999 | Ewart et al. |
| 5,932,410 A | 8/1999 | Whittaker et al. |
| 5,981,207 A | 11/1999 | Burbaum et al. |
| 6,004,530 A | 12/1999 | Sagner et al. |
| 6,030,840 A | 2/2000 | Mullinax et al. |
| 6,033,574 A | 3/2000 | Siddiqi |
| 6,136,549 A | 10/2000 | Feistel |
| 6,174,646 B1 | 1/2001 | Hirai et al. |
| 6,197,537 B1 | 3/2001 | Rao et al. |
| 6,235,464 B1 | 5/2001 | Henderson et al. |
| 6,242,268 B1 | 6/2001 | Wieder et al. |
| 6,243,980 B1 | 6/2001 | Bronstein et al. |
| 6,251,621 B1 | 6/2001 | Lawrence et al. |
| 6,261,779 B1 | 7/2001 | Barbera-Guillem et al. |
| 6,287,798 B1 | 9/2001 | James et al. |
| 6,306,665 B1 | 10/2001 | Buck et al. |
| 6,348,319 B1 | 2/2002 | Braach-Maksvytis et al. |
| 6,362,011 B1 | 3/2002 | Massey et al. |
| 6,387,707 B1 | 5/2002 | Seul et al. |
| 6,402,918 B1 | 6/2002 | Schlenoff et al. |
| 6,444,423 B1 | 9/2002 | Meade et al. |

(Continued)

FOREIGN PATENT DOCUMENTS

| | | |
|---|---|---|
| EP | 0244932 A2 | 11/1987 |
| EP | 0244932 A3 | 11/1987 |

(Continued)

OTHER PUBLICATIONS

Osikowicz, G et al. One-step chromatographic immunoassay for qualitative determination of chorlogonadotropin in urine. Clinical Chemistry. 1990. 36(9): 1586.*
Senior, BW et al. Cleavage of the hormone human chorionic gonadotropin, by the Type 1 IgA1 protease of *Neisseria gonorrhoeae*, and its implications. Journal of Infectious Diseases. 2001. 184: 922-925.*
Abstract of Article entitled *One-step all-in-one dry reagent immunoassays with fluorescent europium chelate label and time-resolved fluorometry*, Lovgren et al. Clinical Chemistry, vol. 42, 1996, pp. 1196-1201.
Abstract of DE10024145A1, Nov. 22, 2001.
Article—*Effect of matrix metalloprotease inhibitors on the 95 kDa metallopeptidase of Candida albicans*, Imbert et al., Journal of Antimicrobial Chemotherapy, vol. 99, 2002, pp. 1007-1010.

(Continued)

*Primary Examiner* — Allison Ford
*Assistant Examiner* — Susan E Fernandez
(74) *Attorney, Agent, or Firm* — Dority & Manning, P.A.

(57) ABSTRACT

A diagnostic test kit for detecting the presence or quantity of an enzyme or enzyme inhibitor is provided. The diagnostic kit utilizes reactive complexes to facilitate the detection of the enzyme or enzyme inhibitor. The reactive complexes include a substrate joined (e.g., covalently bonded, physically adsorbed, etc.) to a reporter and specific binding member. In one embodiment, for example, a peptide, protein, or glycoprotein substrate is joined to a reporter (e.g., dyed latex particle) and specific binding member (e.g., biotinylated compound). In this embodiment, the substrate provides a cleavage target for a proteolytic enzyme. Specifically, upon contacting the reactive complexes, the proteolytic enzyme cleaves the substrate and releases the reporter and/or specific binding member. The signal exhibited by the released reporters may then be used to indicate the presence or quantity of an enzyme or enzyme inhibitor within the test sample.

20 Claims, 3 Drawing Sheets

U.S. PATENT DOCUMENTS

| | | |
|---|---|---|
| 6,451,619 B1 | 9/2002 | Catt et al. |
| 6,468,741 B1 | 10/2002 | Massey et al. |
| 6,472,141 B2 | 10/2002 | Nikiforov |
| 6,485,926 B2 | 11/2002 | Nemori et al. |
| 6,528,321 B1 | 3/2003 | Fitzgerald et al. |
| 6,562,631 B2 | 5/2003 | Braach-Maksvytis et al. |
| 6,582,930 B1 | 6/2003 | Ponomarev et al. |
| 6,585,939 B1 | 7/2003 | Dapprich |
| 6,613,583 B1 | 9/2003 | Richter et al. |
| 6,682,903 B2 | 1/2004 | Saunders |
| 6,720,007 B2 | 4/2004 | Walt et al. |
| 6,916,666 B1 | 7/2005 | Mendel-Hartvig et al. |
| 7,094,528 B2 | 8/2006 | Song et al. |
| 7,521,226 B2 | 4/2009 | Song et al. |
| 7,964,340 B2 * | 6/2011 | Song et al. ........................ 435/4 |
| 2001/0046668 A1 | 11/2001 | Levine et al. |
| 2002/0025541 A1 | 2/2002 | Nelson et al. |
| 2003/0108978 A1 | 6/2003 | Ciambrone et al. |
| 2003/0119073 A1 | 6/2003 | Quirk et al. |
| 2003/0119202 A1 | 6/2003 | Kaylor et al. |
| 2003/0124739 A1 | 7/2003 | Song et al. |
| 2004/0014073 A1 | 1/2004 | Trau et al. |
| 2004/0029205 A1 | 2/2004 | Small, Jr. et al. |
| 2004/0043502 A1 | 3/2004 | Song et al. |
| 2004/0043507 A1 | 3/2004 | Song et al. |
| 2004/0043511 A1 | 3/2004 | Song et al. |
| 2004/0043512 A1 | 3/2004 | Song et al. |
| 2004/0081971 A1 | 4/2004 | Yue et al. |
| 2004/0096918 A1 | 5/2004 | Martin et al. |
| 2004/0121480 A1 | 6/2004 | Wei et al. |
| 2005/0112780 A1 | 5/2005 | Song |
| 2006/0003394 A1 | 1/2006 | Song |

FOREIGN PATENT DOCUMENTS

| | | |
|---|---|---|
| EP | 0297290 A2 | 1/1989 |
| EP | 1422525 A1 | 5/2004 |
| WO | WO 8804777 A1 | 6/1988 |
| WO | WO 9964864 A1 | 12/1999 |
| WO | WO 0163299 A1 | 8/2001 |
| WO | WO 03023051 A2 | 3/2003 |
| WO | WO 03023051 A3 | 3/2003 |
| WO | WO 03085403 A1 | 10/2003 |
| WO | WO 2005066359 A1 | 7/2005 |
| WO | WO 2006079826 A1 | 8/2006 |
| WO | WO 2007096637 A1 | 8/2007 |
| WO | WO 2007128980 A1 | 11/2007 |

OTHER PUBLICATIONS

Article—*Protease and Protease Inhibitor Assays Using Biotinylated Casein Coated on a Solid Phase*, Gan et al., Analytical Biochemistry. vol. 268, 1999, pp. 151-156.

Article—*Quenched BODIPY Dye-Labeled Casein Substrates for the Assay of Protease Activity by Direct Fluorescence Measurement*, Jones et al., Analytical Biochemistry, vol. 251, 1997, pp. 144-152.

Article—*Solid Substrate Phosphorescent Immunoassay Based on Bioconjugated Nanoparticles*, Sun et al., Analytical Letters, vol. 34, No. 10, 2001, pp. 1627-1637.

Article—*Bioseparations Engineering Principles, Practice, and Economics*, Michael R. Ladisch, 2001, John Wiley & Sons, Inc., p. 200.

Paper—Section 10.4—Detecting Peptidases and Proteases, 19 pages, May 2004, www.probes.com/handbook.

Product Description for BioMag® Carboxyl-terminated Particles from Bangs Laboratories, Inc., 2 pages, Jan. 2004.

Product Description for EnzChek™ Protease Assay Kits from Molecular Probes, 3 pages, May 2004.

Product Description for EZ-Link NHS-PEO Solid Phase Biotinylation Kit from Pierce, 4 pages, May 2004.

Product Description for EZ-Link® Sulfo-NHS-Biotin Reagents from Pierce, 5 pages, Feb. 2004.

Product Description for Fluorescence Microplate Assays from Molecular Probes, 112 pages, 2002.

Product Information on Enzymatic Assay of Protease[1] Casein as a Substrate from Sigma, 4 pages, 1999.

Search Report and Written Opinion for PCT/US2005/011051, Sep. 19, 2005.

* cited by examiner

ENZYMATIC DETECTION TECHNIQUES

RELATED APPLICATIONS

The present application is a divisional of U.S. application Ser. No. 10/882,108, filed on Jun. 30, 2004, which is incorporated herein in its entirety by reference thereto for all purposes.

BACKGROUND OF THE INVENTION

It is often desirable to determine the presence or quantity of a particular enzyme within a test sample. In some cases, the mere presence of an enzyme may, for example, indicate the existence of tissue or organ damage. Likewise, abnormal enzyme concentrations may also indicate other conditions, such as a bacterial or viral infection. For instance, proteases (e.g., aspartic proteases) and metallopeptidases are believed to increase the pathogenicity of *Candida albicans,* a microorganism that may cause candidal vaginitis ("yeast infection"). The presence or concentration of an enzyme in a test sample may also serve as a diagnostic marker for some types of cancers and other conditions. For instance, prostate-specific antigen (PSA) is a well-known marker for prostate cancer. Other examples of diagnostic markers include cathepsin B (cancer), cathepsin G (emphysema, rheumatoid arthritis, inflammation), plasminogen activator (thrombosis, chronic inflammation, cancer), and urokinase (cancer).

One conventional technique for detecting the presence of an enzyme is described in U.S. Pat. No. 6,348,319 to Braach-Maksvytis, et al. Braach-Maksvytis, et al. functions by sensing the digestion of a substrate by the enzyme. For example, FIG. 1 of Braach-Maksvytis, et al. illustrates a device 10 that includes a first zone 11 and a second zone 12. The first zone 11 is provided with polymer beads 13 (carrier) linked to streptavidin 14 (reporter) via a peptide linker 15 that is cleavable by a protease 16. Upon addition of the protease 16, the streptavidin 14 is released and passes to the second zone 12, which includes a biosensor membrane 17 that detects the presence of streptavidin through a change in the impedance of the membrane. (Col. 5, ll. 25-30). Unfortunately, however, techniques such as described by Braach-Maksvytis, et al., are far too complex and cost prohibitive for certain types of applications, such as those requiring a relatively quick diagnosis by a patient (self-diagnosis or with the aid of medical personnel).

As such, a need currently exists for a simple and inexpensive technique to accurately detect the presence of an enzyme within a test sample.

SUMMARY OF THE INVENTION

In accordance with one embodiment of the present invention, a diagnostic kit is disclosed for detecting an enzyme, or an inhibitor thereof, within a test sample. The kit comprises a plurality of reactive complexes that each comprises a substrate joined to a reporter and specific binding member. The substrate is cleavable by an enzyme (e.g., hydrolytic enzyme). In one embodiment, for example, the reporter includes a particle labeled with a detectable substance. The kit further comprises a chromatographic medium (e.g., porous membrane) that is capable of being placed in communication with the test sample. The chromatographic medium defines a first detection zone within which the specific binding member is capable of being captured. A first detection signal is capable of being generated within the first detection zone, such as by reporters immobilized therein. The intensity of the first detection signal may be inversely proportional to the amount of an enzyme within the test sample, and may likewise be directly proportional to the amount of an enzyme inhibitor within the test sample.

In certain embodiments, the chromatographic medium may further comprise a second detection zone within which the reporter is capable of being captured. For example, in one embodiment, a receptive material is immobilized within the second detection zone that has an affinity for the reporter. A second detection signal is capable of being generated within the second detection zone, such as by reporters immobilized therein. The intensity of the second detection signal may directly proportional to the amount of an enzyme within the test sample, and may likewise be inversely proportional to the amount of an enzyme inhibitor within the test sample.

In accordance with another embodiment of the present invention, a method for detecting an enzyme, or an inhibitor thereof, within a test sample, is disclosed. The method comprises contacting a test sample with a plurality of reactive complexes to form an incubation mixture, the reactive complexes each comprising a substrate joined to a reporter and specific binding member. The substrate is cleavable by an enzyme to release the reporter and the specific binding member, the reporter being capable of directly or indirectly generating a detection signal. The method further comprises applying the incubation mixture to a chromatographic medium, the chromatographic medium defining a first detection zone within which the specific binding member is capable of being captured. The presence or intensity of the detection signal within the first detection zone is determined.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
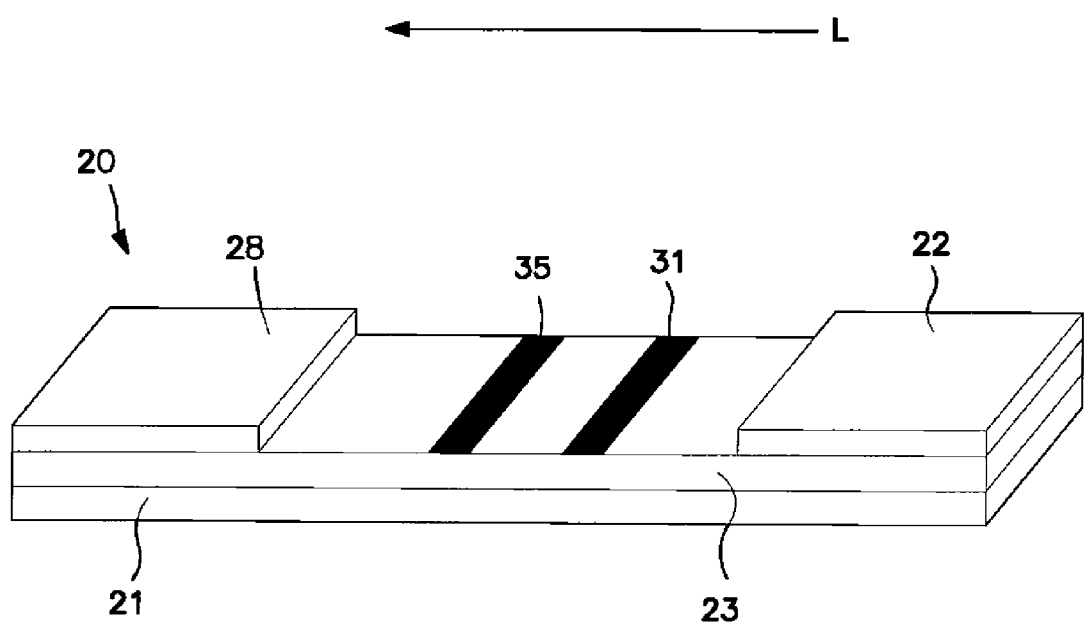
FIG. 1 is a perspective view of one embodiment of an assay device that may be used in the diagnostic test kit of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "test sample" generally refers to a material suspected of containing an enzyme and/or enzyme inhibitor. For example, the test sample may be obtained or derived from a biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid, and so forth. Besides physiological fluids, other liquid samples may be used such as water, food products, and so forth, for the performance of environmental or food production assays. In addition, a solid material may be used as the test sample. The test sample may be used directly as obtained from a source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, etc. Moreover, it may also be beneficial to modify a solid test sample to form a liquid medium, to release the enzyme and/or enzyme inhibitor, etc.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

The present invention is generally directed to a diagnostic test kit for detecting the presence or quantity of an enzyme or enzyme inhibitor. The diagnostic kit utilizes reactive complexes to facilitate the detection of the enzyme or enzyme inhibitor. The reactive complexes include a substrate joined (e.g., covalently bonded, physically adsorbed, etc.) to a reporter and specific binding member. In one embodiment, for example, a peptide, protein, or glycoprotein substrate is joined to a reporter (e.g., dyed latex particle) and specific binding member (e.g., biotinylated compound). In this embodiment, the substrate provides a cleavage target for a proteolytic enzyme. Specifically, upon contacting the reactive complexes, the proteolytic enzyme cleaves the substrate and releases the reporter and/or specific binding member. The signal directly or indirectly generated by the released reporters may then be used to indicate the presence or quantity of an enzyme or enzyme inhibitor within the test sample.

Various types of enzymes may be detected in accordance with the present invention. For instance, transferases, hydrolases, lyases, and so forth, may be detected. In some embodiments, the enzyme of interest is a "hydrolase" or "hydrolytic enzyme", which refers to enzymes that catalyze hydrolytic reactions. Examples of such hydrolytic enzymes include, but are not limited to, proteases, peptidases, lipases, nucleases, homo- or hetero-oligosaccharidases, homo- or hetero-polysaccharidases, phosphatases, sulfatases, neuraminidases and esterases. In one embodiment, for example, peptidases may be detected. "Peptidases" are hydrolytic enzymes that cleave peptide bonds found in shorter peptides. Examples of peptidases include, but are not limited to, metallopeptidases; dipeptidylpeptidase I, II, or IV; and so forth. In another embodiment, proteases may be detected. "Proteases" are hydrolytic enzymes that cleave peptide bonds found in longer peptides and proteins. Examples of proteases that may be detected according to the present invention include, but are not limited to, serine proteases (e.g., chymotrypsin, trypsin, elastase, PSA, etc.), aspartic proteases (e.g., pepsin), thiol proteases (e.g., prohormone thiol proteases), metalloproteases, acid proteases, and alkaline proteases. Still other enzymes are described in U.S. Pat. No. 6,243,980 to Bronstein, et al. and 2004/0081971 to Yue, et al., which are incorporated herein in their entirety by reference thereto for all purposes.

Likewise, any of a variety of known enzyme inhibitors may also be detected in accordance with the present invention. For example, known inhibitors of hydrolytic enzymes include, but are not limited to, inhibitors of proteases, peptidases, lipases, nucleases, homo- or hetero-oligosaccharidases, homo- or hetero-polysaccharidases, phosphatases, sulfatases, neuraminidases and esterases. Protease inhibitors may include, for instance, aspartic protease inhibitors, serine protease inhibitors, thiol protease inhibitors, metalloprotease inhibitors, acid or alkaline protease inhibitors, and so forth. Some specific examples of protease inhibitors include benzamideine, indole, pepstatin, ovomacroglobulin, haloperidol, transition state mimetics, and so forth.

As stated above, reactive complexes are used in the present invention to detect the presence or quantity of an enzyme or enzyme inhibitor. The reactive complexes include a substrate joined to a reporter and specific binding member. The term "substrate" generally refers to a substance that is chemically acted upon by an enzyme to form a product. The substrate may occur naturally or be synthetic. Some suitable substrates for hydrolytic enzymes include, for instance, esters, amides, peptides, ethers, or other chemical compounds having an enzymatically-hydrolyzable bond. The enzyme-catalyzed hydrolysis reaction may, for example, result in a hydroxyl or amine compound as one product, and a free phosphate, acetate, etc., as a second product. Specific types of substrates may include, for instance, proteins or glycoproteins, peptides, nucleic acids (e.g., DNA and RNA), carbohydrates, lipids, esters, derivatives thereof, and so forth. For instance, some suitable substrates for peptidases and/or proteases may include peptides, proteins, and/or glycoproteins, such as casein (e.g., β-casein, azocasein, etc.), albumin (e.g., bovine serum albumin (BSA)), hemoglobin, myoglobin, keratin, gelatin, insulin, proteoglycan, fibronectin, laminin, collagen, elastin, and so forth. Still other suitable substrates are described in U.S. Pat. No. 4,748,116 to Simonsson, et al.; U.S. Pat. No. 5,786,137 to Diamond, et al.; U.S. Pat. No. 6,197,537 to Rao, et al.; and U.S. Pat. No. 6,235,464 to Henderson, et al.; U.S. Pat. No. 6,485,926 to Nemori, et al., which are incorporated herein in their entirety by reference thereto far all purposes.

The specific binding member may generally be any member of a specific binding pair, i.e., two different molecules where one of the molecules chemically and/or physically binds to the second molecule. For instance, immunoreactive specific binding members may include antigens, haptens, antibodies (primary or secondary), and complexes thereof, including those formed by recombinant DNA methods or peptide synthesis. An antibody may be a monoclonal or polyclonal antibody, a recombinant protein or a mixtures) or fragment(s) thereof, as well as a mixture of an antibody and other specific binding members. The details of the preparation of such antibodies and their suitability for use as specific binding members are well known to those skilled in the art. Other common specific binding members include, but are not limited to, biotin and avidin, streptavidin, neutravidin, captavidin, or an anti-biotin antibody; protein A and G; carbohydrates and lectins, complementary nucleotide sequences (including probe and capture nucleic acid sequences used in DNA hybridization assays to detect a target nucleic acid sequence); complementary peptide sequences including those formed by recombinant methods; effector and receptor molecules; hormone and hormone binding protein; enzyme cofactors and enzymes, enzyme inhibitors and enzymes;

derivatives thereof, and so forth. Furthermore, specific binding pairs may include members that are analogs, derivatives, and/or fragments of the original specific binding member.

In addition to being joined to a specific binding member, such as described above, the substrate is also joined to a reporter to form the reactive complexes. The reporters may contain any substance capable of directly or indirectly generating a detectable signal. Suitable detectable substances may include, for instance, chromogens; luminescent compounds (e.g., fluorescent, phosphorescent, etc.); radioactive compounds; visual compounds (e.g., latex or metallic particles, such as gold); liposomes or other vesicles containing signal-producing substances; enzymes and/or substrates, and so forth. For instance, some enzymes suitable for use as detectable substances are described in U.S. Pat. No. 4,275,149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable reporters may be described in U.S. Pat. No. 5,670,381 to Jou, et al. and U.S. Pat. No. 5,252,459 to Tarcha, et al., which are incorporated herein in their entirety by reference thereto for all purposes.

In some embodiments, the reporters may contain a luminescent compound that produces an optically detectable signal. The luminescent compound may be a molecule, polymer, dendrimer, particle, and so forth. For example, suitable fluorescent molecules may include, but not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or nonaqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine]2-[3-(4-methyl-2,2'-bipyridine-4-yl)propyl]-1,3-dioxolane ruthenium (II); bis(2,2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2,2'bipyridine)ruthenium (II); (2,2'-bipyridine)[bis-bis(1,2-diphenylphosphino)ethylene]2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2,2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, "time-resolved" luminescent detection techniques are utilized. Time-resolved detection involves exciting a luminescent compound with one or more short pulses of light, then typically waiting a certain time (e.g., between approximately 1 to 100 microseconds) after excitation before measuring the remaining the luminescent signal. In this manner, any short-lived phosphorescent or fluorescent background signals and scattered excitation radiation are eliminated. This ability to eliminate much of the background signals may result in sensitivities that are 2 to 4 orders greater than conventional fluorescence or phosphorescence. Thus, time-resolved detection is designed to reduce background signals from the emission source or from scattering processes (resulting from scattering of the excitation radiation) by taking advantage of the characteristics of certain luminescent materials.

To function effectively, time-resolved techniques generally require a relatively long emission lifetime for the luminescent compound. This is desired so that the compound emits its signal well after any short-lived background signals dissipate. Furthermore, a long luminescence lifetime makes it possible to use low-cost circuitry for time-gated measurements. For example, the detectable compounds may have a luminescence lifetime of greater than about 1 microsecond, in some embodiments greater than about 10 microseconds, in some embodiments greater than about 50 microseconds, and in some embodiments, from about 100 microseconds to about 1000 microseconds. In addition, the compound may also have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, one suitable type of fluorescent compound for use in time-resolved detection techniques includes lanthanide chelates of samarium (Sm (III)), dysprosium (Dy (III)), europium (Eu (III)), and terbium (Tb (III)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have exceptionally large Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent compound. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-Eu$^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N,N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent compounds described above, other compounds that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; and U.S. Pat. No. 5,637,509 to Hemmila, et al., which are incorporated herein in their entirety by reference thereto for all purposes.

As stated, the reporter may indirectly generate a detectable signal in some embodiments of the present invention. In such instances, the reporter may not specifically contain a detectable substance, but instead be capable of interacting with a detectable substance to generate a detection signal. For example, in some embodiments, the reporter may be a member of a specific binding pair, such as described above. For example, a reporter that is a member of a specific binding pair may be placed into contact with a probe conjugated with another member of the specific binding pair. Thus, the released reporter will bind to the conjugated probe, which may then be readily detected (directly or indirectly) using techniques well known to those skilled in the art. As will be explained in more detail below, when the reporter contains a specific binding member, it is generally desired that the specific binding member is different than and has no specific binding affinity for the other specific binding member joined to the substrate.

Whether or not the reporter directly or indirectly generates a signal, it may contain particles (sometimes referred to as "beads" or "microbeads"). Among other things, particles enhance the ability of the reporter to travel through a chromatographic medium and become immobilized within a detection zone, such as described below. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex particles are labeled with a fluorescent or colored dye. Although any latex particle may be used, the latex particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al. and U.S. Pat. No. 5,252,459 to Tarcha, et al. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. of Eugene, Oreg. In addition, commercially available examples of suitable colored, latex microparticles include carboxylated latex beads sold by Bangs Laboratories, Inc. of Fishers, Ind.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

The specific binding member and reporter may generally be attached to the substrate using any of a variety of well-known techniques. For instance, covalent attachment of the specific binding member and/or reporter to a substrate may be accomplished using carboxylic, amino, aldehyde, bromoacetyl, iodoacetyl, thiol, epoxy and other reactive functional groups, as well as residual free radicals and radical cations, through which a coupling reaction may be accomplished. A surface functional group may also be incorporated as a functionalized co-monomer because the surface of the reporter may contain a relatively high surface concentration of polar groups. In certain cases, the specific binding member and/or reporter may be capable of direct covalent bonding to a substrate without the need for further modification. It should also be understood that, besides covalent bonding, other attachment techniques, such as physical adsorption, may also be utilized in the present invention. Still other non-covalent linkage techniques may employ antibodies and/or antigens, such as secondary antibodies (e.g., avidin, streptavidin, neutravidin, and/or biotin).

One particular technique for covalently bonding a reporter and specific binding member to a substrate will now be described in more detail. In this particular embodiment, the substrate is β-casein, the reporter is a dyed particle, and the specific binding member is a biotin derivative. For example, the reporter may be red carboxylated latex particles available from Molecular Probes, Inc. under the name "FluoSphere." Likewise, the specific binding member may be sulfosuccinimidyl-6-(biotin-amido)hexanoate, which is available from Pierce Biotechnology, Inc. of Rockford, Ill. under the name EZ-Link® Sulfo-NHS-LC-Biotin. Techniques employed in making such NHS-activated biotins are believed to be described in U.S. Pat. No. 5,872,261 to Bremmer, et al., which is incorporated herein in its entirety by reference thereto for all purposes.

Figure 2:
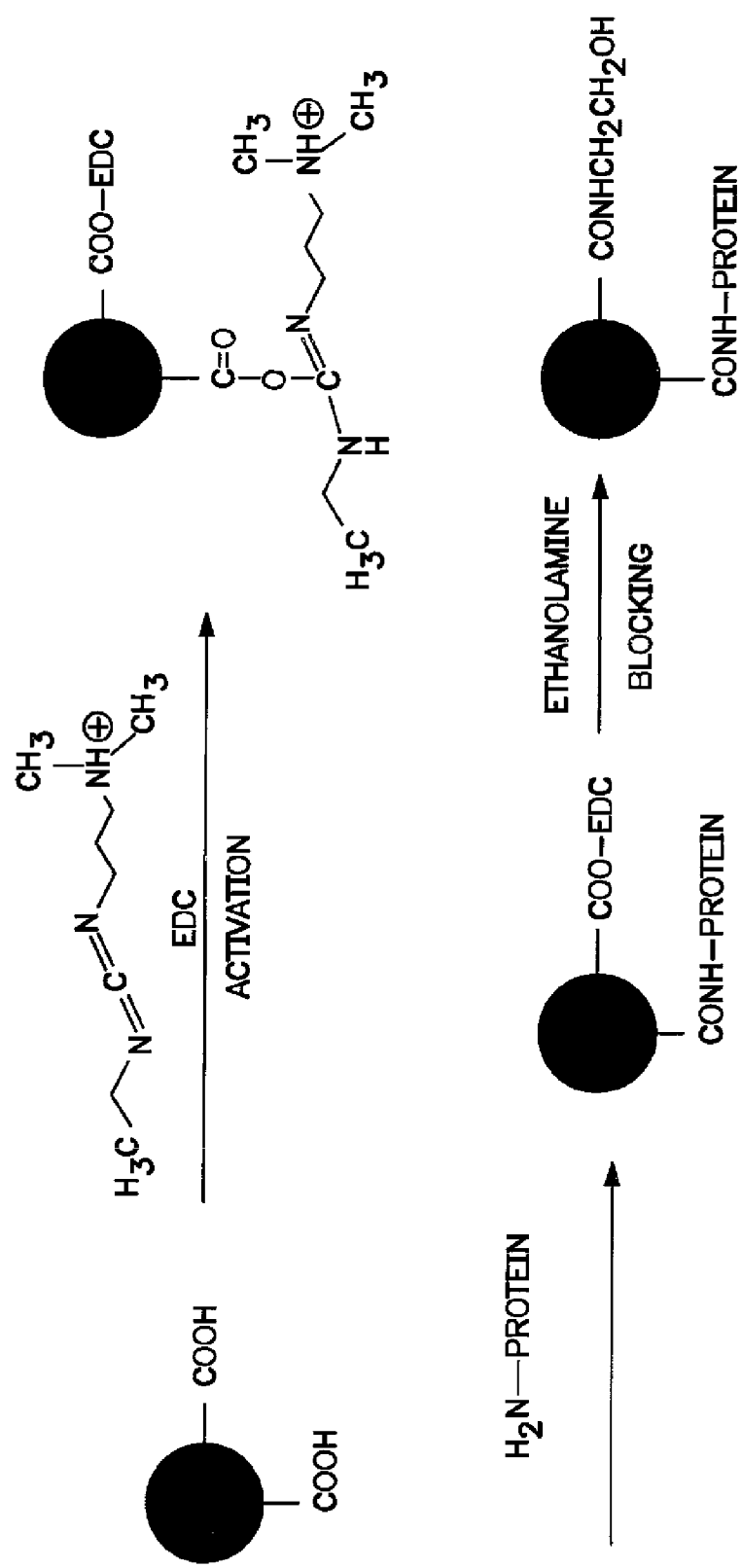
FIG. 2 is a graphical illustration of one embodiment for covalently bonding a reporter to a substrate.

To covalently conjugate the dyed particle with β-casein, the carboxylic groups on the particle surface are first activated with a carbodiimide (e.g., ethylcarbodiimide hydrochloride (EDC)), such as shown in FIG. 2. Because protein and glycoprotein substrates (e.g., β-casein) typically possess primary amine groups ($NH_2$), such as on the side chain of lysine (K) residues and/or the N-terminus of each polypeptide, the activated carboxylic acid groups may then be reacted with the primary amine (—$NH_2$) groups of the substrate to form an amide bond. This reaction may occur in a buffer, such as phosphate-buffered saline (PBS) (e.g., pH of 7.2), 2-(N-morpholino) ethane sulfonic acid (MES) (e.g., pH of 5.3), or borate buffer (e.g., pH of 8.5). If desired, the resulting reactive complexes may then be blocked with ethanolamine, for instance, to block any remaining activated sites.

In a somewhat similar manner, the biotin-based specific binding member may also be covalently bonded to β-casein. For example, NHS-activated biotins may form covalent amide bonds with the primary amine groups present on the substrate (optionally in the presence of a buffer). An example of such a reaction is set forth below:

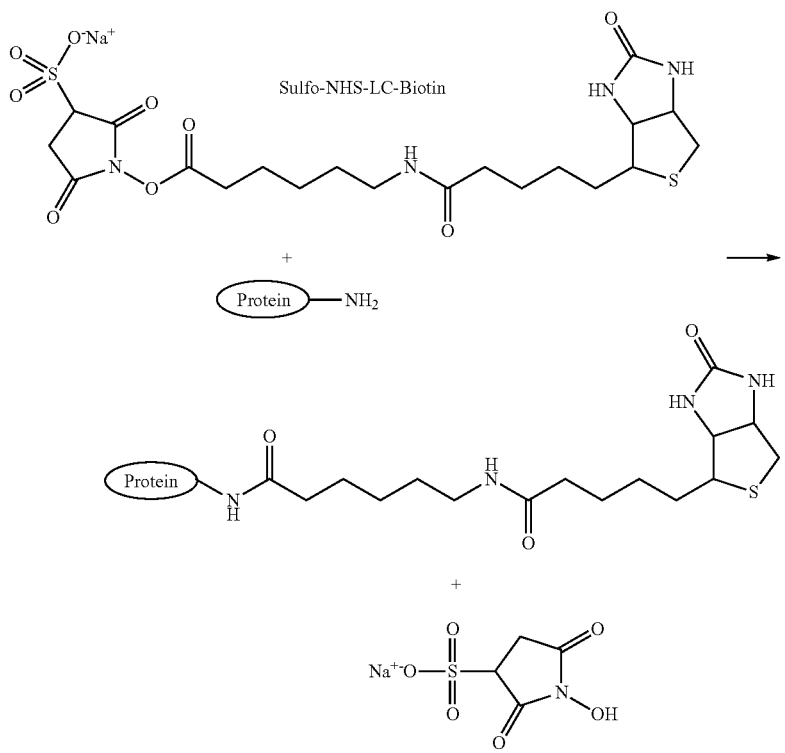

Once formed, a user may allow the test sample to incubate with the reactive complexes for a certain period of time. For example, those skilled in the art readily recognize that the time of incubation for an enzyme-catalyzed reaction depends on the activity of the enzyme of interest, which in turn depends on in part on the temperature, pH, substrate concentration, the presence of inhibitors (competitive (binds to enzyme), uncompetitive (binds to enzyme-substrate complex), or noncompetitive (binds to enzyme and/or enzyme-substrate complex)), and so forth. These factors may be selectively controlled as desired to increase or decrease the incubation time. For example, the time for incubation may be greater than about 1 minute, in some embodiments from about 5 to about 50 minutes, and in some embodiments, from about 10 to about 25 minutes. Likewise, the pH may be selectively controlled to facilitate enzyme activity. For example, high levels of basic substances within a test sample may result in a pH that is too high for optimum activity of some enzymes, e.g., greater than 8. Specifically, an enzyme may possess optimum activity at a pH level of from about 3 to about 8, and in some embodiments, from about 4 to about 7. Thus, if desired, a buffer or other pH-altering compound may be employed to maintain the desired pH.

After incubation, any enzyme present within the test sample will typically cleave the substrate of at least a portion of the reactive complexes. As a result, various species may be formed, including released reporters, released specific binding members, partially cleaved complexes (e.g., enzyme-reporter-substrate-specific binding member), and unreacted complexes (e.g., reporter-substrate-specific binding member). Longer incubation times and greater enzyme concentrations may result in a greater concentration of released reporters and specific binding members in the resulting incubation mixture. Further, it should be understood that the "released" reporters and specific binding members may or may not contain fragments of the complex depending on the nature of the substrate and enzyme. For instance, when using longer chain substrates (e.g., proteins), the released reporters and specific binding members may contain peptide fragments from the protein substrate. On the other hand, when using shorter chain substrates (e.g., peptides), the released reporters and specific binding members may be relatively free of such fragments.

In accordance with the present invention, the diagnostic test kit also contains an assay device that is used to indicate the presence or absence of reporters. The assay device employs a chromatographic medium for chemically separating the released reporters from other species present within the incubation mixture. In contrast to other separation techniques, such as centrifugation, the present inventor has discovered that a chromatographic medium may simplify and reduce the costs of the resulting diagnostic test kit for many consumer applications, including those in which a disposable kit is desired.

Referring to FIG. 1, for instance, one embodiment of an assay device 20 that may be used to indicate the presence or quantity of an enzyme in accordance with the present invention will now be described in more detail. As shown, the assay device 20 contains a chromatographic medium 23 optionally carried by a support 21. The chromatographic medium 23 may be made from any of a variety of materials through which a fluid is capable of passing, such as a fluidic channel, porous membrane, etc. For example, the chromatographic medium 23 may be a porous membrane formed from materials such as, but not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The support 21 may be formed from any material able to carry the chromatographic medium 23. Although not required, the support 21 may be transparent so that light readily passes therethrough. In addition, it is also generally desired that the support 21 is liquid-impermeable so that fluid flowing through the medium does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. As is well known the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate structures are described in U.S. Pat. No. 5,075,077 to Durley, III, et al., which is incorporated herein in its entirety by reference thereto for all purposes.

The assay device 20 may also utilize an absorbent material 28. The absorbent material 28 generally receives fluid that has migrated through the entire chromatographic medium 23. As is well known in the art, the absorbent material 28 may assist in promoting capillary action and fluid flow through the medium 23.

The above-described incubation process may be conducted before applying the test sample to the chromatographic medium 23, or it may be incorporated as part of the assaying procedure (i.e., incubation occurs after the test sample is applied, such as within an incubation well). For instance, the incubation mixture may be directly applied to a portion of the chromatographic medium 23 through which it may then travel in the direction illustrated by arrow "L" in FIG. 1. Alternatively, the mixture may first be applied to a sample pad 22 or other material that is in fluid communication with the chromatographic medium 23. Some suitable materials that may be used to form the sample pad 22 include, but are not limited to, nitrocellulose, cellulose, porous polyethylene pads, and glass fiber filter paper. If desired, the sample pad 22 may also contain one or more assay pretreatment reagents, either diffusively or non-diffusively attached thereto.

Regardless, the chromatographic medium 23 defines a first detection zone 31 within which the specific binding members may be captured and detected (e.g., indirectly). For example, in one embodiment, a first receptive material is immobilized within the first detection zone 31 that serves as a stationary binding site for released specific binding members, specific binding members present on unreacted complexes, or specific binding members present on partially cleaved complexes. For example, in some embodiments, the first receptive material may be a biological receptive material. Such biological receptive materials are well known in the art and may include, but are not limited to, antibodies, antigens, haptens, biotin, avidin, streptavidin, neutravidin, captavidin, protein A, protein G, carbohydrates, lectins, nucleotide sequences, peptide sequences, effector and receptor molecules, hormone and hormone binding protein, enzyme cofactors and enzymes, enzyme inhibitors and enzymes, and derivatives thereof. As the enzyme concentration begins to increase in the test sample, more reporters are released that have little or no specific binding affinity for the receptive material at the first detection zone 31. The reduced quantity of reporters at the first detection zone 31 thus results in a decrease in signal intensity. From this decrease in signal intensity, the presence or concentration of the enzyme may be readily determined. For example, in one embodiment, the amount of enzyme is inversely proportional to the signal intensity at the first detection zone 31, $I_1$. If desired, the signal intensity $I_1$ may be plotted versus the enzyme concentration for a range of known enzyme concentrations to generate an intensity curve. To determine the quantity of enzyme in an unknown test sample, the signal intensity may then be converted to enzyme concentration according to the intensity curve.

The first detection zone 31 may generally provide any number of distinct detection regions so that a user may better determine the concentration of an enzyme within a test sample. Each region may contain the same or different receptive materials. For example, the detection zone 31 may include two or more distinct detection regions (e.g., lines, dots, etc.). The use of two or more distinct detection regions may provide certain benefits, such as facilitating semi-quantitation and/or inhibiting potential false positives due to over-running of the reactive complexes or other materials. The detection regions may be disposed in the form of lines in a direction substantially perpendicular to the flow of the test sample through the chromatographic medium 23. Likewise, in some embodiments, the detection regions may be disposed in the form of lines in a direction substantially parallel to the flow of the test sample through the medium 23. It should be understood that one or more distinct regions of the first detection zone 31 may exhibit the above-described relationship between signal intensity and enzyme concentration; however, each distinct region need not exhibit such a relationship. For example, in some embodiments, only one of multiple distinct regions may exhibit a signal intensity that is inversely proportional to the concentration of the enzyme. The signal intensity of other distinct regions, such as those used to reduce false positives, may otherwise remain constant, or exhibit an increase and/or decrease in signal intensity. So long as at least one distinct region of the detection zone 31 satisfies the inverse relationship, the signal intensity exhibited by the first detection zone 31 is considered inversely proportional to the enzyme concentration.

In accordance with the present invention, the level of detection sensitivity for the enzyme of interest may be selectively controlled depending on the desired application. One particular technique for controlling the detection sensitivity involves manipulating the quantity of the first receptive material used in the first detection zone 31. For instance, when assaying samples suspected of containing large concentrations of an enzyme, the quantity of the first receptive material may be equal to or greater than the minimum required to capture the total quantity of reactive complexes utilized. Thus, if no enzyme were present in the test sample, all of the reactive complexes would become immobilized at the detection zone 31 and all of the reporters would be present within the first detection zone 31. The minimum quantity required to capture all of the reactive complexes may be determined experimentally, and generally depends upon the amount of the reactive complexes used and the binding affinity between the first receptive material and the specific binding member.

In applications where enhanced detection sensitivity is desired (e.g., low suspected enzyme concentrations or short incubation times), the quantity of the first receptive material may be less than the minimum required to capture the total quantity of reactive complexes utilized. The use of such a limited quantity of the first receptive material may provide a variety of benefits, including decreasing the likelihood that any partially cleaved complexes are captured at the first detection zone 31, which would otherwise result in a measured enzyme concentration that is slightly lower than the actual concentration. That is, as the concentration of the enzyme increases, more specific binding members are released from the reactive complexes. Due to their smaller molecular size, these released specific binding members generally reach the first detection zone 31 faster than the partially cleaved complexes and unreacted complexes, and thus have a higher probability of occupying the available binding sites. Further, the partially cleaved complexes also generally contain a lesser quantity of specific binding members than those that are completely unreacted. This reduction in the quantity of specific binding members statistically decreases the chance that the partially cleaved complexes will bind to the first detection zone 31.

As discussed above, the inverse relationship between enzyme concentration and signal intensity may be correlated to the actual enzyme concentration in the test sample. However, because it is not always desirable to use an assay format that correlates an "increase" in enzyme concentration to a "decrease" in signal intensity (e.g. consumer applications), the present invention also provides for embodiments in which an "increase" in enzyme concentration is directly correlated to an "increase" in signal intensity. In such cases, additional detection zones may be utilized. For example, referring again to FIG. 1, the chromatographic medium 23 may also define a second detection zone 35 positioned downstream from the first detection zone 31. The second detection zone 35 may provide one or more distinct regions (e.g., line, dot, etc.), and may be positioned at any orientation relative to the flow of the test sample.

Within the second detection zone 35, any released reporters, partially cleaved complexes, or unreacted complexes that do not bind to the first receptive material at the detection zone 31 may be captured and detected. The manner in which the released reporters are captured may depend on the nature of the reporters utilized. In some embodiments, a second receptive material may be immobilized within the second detection zone 35 for capturing reporters. For example, the second receptive material may be a biological receptive material, such as, but not limited to, antibodies, antigens, haptens, biotin, avidin, streptavidin, neutravidin, captavidin, protein A, protein G, carbohydrates, lectins, nucleotide sequences, peptide sequences, effector and receptor molecules, hormone and hormone binding protein, enzyme cofactors and enzymes, enzyme inhibitors and enzymes, and derivatives thereof. Because the second receptive material desirably binds specifically to the reporters, it is normally different than the first receptive material.

For example, the released reporter may be conjugated with a specific binding member selected to have an affinity for the second receptive material within the second detection zone 35. The specific binding member may be conjugated to the reporter using any of a variety of well-known techniques, such as through covalent bonding and/or physical adsorption in a manner such as described above. In one particular embodiment, carboxylic groups of the reporter are activated and reacted with amino groups of an antibody to form an amide bond. In this instance, the released reporter may become immobilized within the second detection zone 35 through specific binding between the antibody and a receptive material so that the signal generated by the detectable substance may be detected. For example, the first receptive material may be a secondary antibody (such as an anti-biotin antibody, e.g., goat anti-Mouse IgG antibody), avidin (a highly cationic 66,000-dalton glycoprotein), streptavidin (a nonglycosylated 52,800-dalton protein), neutravidin (a deglysolated avidin derivative), or captavidin (a nitrated avidin derivative). In this embodiment, the first receptive material may bind to a biotin (Mouse IgG antibody) specific binding member. The reporter may, for instance, be a fluorescent-dyed particle conjugated with C-reactive protein, which may bind to a monoclonal antibody second receptive material (e.g., anti C-reactive protein (CRP) monoclonal antibody).

Of course, any other suitable technique for capturing and detection the released reporters may also be used. For example, in some embodiments, non-biological receptive materials may be immobilized within the second detection zone 35 for capturing released reporters. Such non-biological receptive materials may be particularly useful in capturing, for example, released reporters that contain labeled particles. For instance, in one embodiment, the receptive material is a polyelectrolyte. Polyelectrolytes may have a net positive or negative charge, as well as a net charge that is generally neutral. Some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized in the present invention, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly (styryl-b-acrylic acid), both of which are available from Polymer Source, Inc. of Dorval, Canada. Further examples of polyelectrolytes are described in more detail in U.S. Patent App. Publication No. 2003/0124739 to Song, et al., which is incorporated herein in it entirety by reference thereto for all purposes, Although any polyelectrolyte may generally be utilized, the polyelectrolyte selected for a particular application may vary depending on the nature of the released reporters. In particular, the distributed charge of a polyelectrolyte allows it to bind to substances having an opposite charge. Thus, for example, polyelectrolytes having a net positive charge are often better equipped to bind with released reporters (e.g., dyed particles) that are negatively charged, while polyelectrolytes that have a net negative charge are often better equipped to bind to released reporters that are positively charged. Thus, in such instances, the ionic interaction between these molecules allows the required binding to occur within the second detection zone 35. Nevertheless, although ionic interaction is primarily utilized to achieve the desired binding, it has also been discovered that polyelectrolytes may bind with reporters having a similar charge.

Besides using receptive materials, other capturing techniques may also be utilized. For example, in one embodiment, the reporter may contain a magnetic substance that is capable of being captured by a magnetic device. Generally, a material is considered "magnetic" or "magnetically responsive" if it is influenced by the application of a magnetic field, such as, for example, if it is attracted or repulsed or has a detectable magnetic susceptibility or induction. For instance, some examples of suitable magnetically responsive substances that may be used to impart magnetic properties include, but are not limited to, paramagnetic materials, superparamagnetic materials, ferromagnetic materials, ferrimagnetic materials, and metamagnetic materials. Specific examples are metals such as iron, nickel, cobalt, chromium, and manganese; lanthanide elements, such as neodymium, erbium; alloys, such as magnetic alloys of aluminum, nickel, cobalt, or copper; oxides, such as ferric oxide ($Fe_3O_4$), ferrous oxide ($Fe_2O_3$), chromium oxide ($CrO_2$), cobalt oxide (CoO), nickel oxide ($NiO_2$), or manganese oxide ($Mn_2O_3$); composite materials, such as ferrites; and solid solutions, such as magnetite with ferric oxide. In some embodiments, the reporter contains a magnetic particle that is dyed with a detectable substance, such as described above.

In one embodiment, the magnetic device is positioned adjacent to (e.g., below) the second detection zone 35 defined by the chromatographic medium 23. In this manner, the magnetic device may immobilize the released reporters, as well as any partially cleaved or unreacted complexes, within the second detection zone 35. Any magnetic device may be used in the present invention. A magnetic field generator, for instance, may be used to generate a magnetic field that elicits a response from the magnetic substances. Suitable magnetic field generators include, but are not limited to, permanent magnets and electromagnets. Some commercially available examples of suitable magnetic separation devices include the Dynal MPC series of separators manufactured by Dynal, Inc. of Lake Success, N.Y., which employ a permanent magnet located externally to a container holding a test medium. Still other magnetic devices may be described in U.S. Pat. Nos. 5,200,084 to Liberti, et al.; U.S. Pat. No. 5,647,994 to Tuunanen, et al.; U.S. Pat. No. 5,795,470 to Wang, et al.; and U.S. Pat. No. 6,033,574 to Siddiqi, which are incorporated herein in their entirety by reference thereto for all purposes.

When the reporters contain a substance that is directly detectable, an increase in enzyme concentration results in an increase in the signal intensity at the second detection zone 35, $I_2$, due to the presence of released reporters and/or partially cleaved complexes. From this increase in signal intensity, the presence or concentration of the enzyme may be readily determined. For example, in one embodiment, the amount of enzyme is directly proportional to the signal intensity at the second detection zone 35, $I_2$. If desired, the signal intensity $I_2$ may be plotted versus the enzyme concentration for a range of known enzyme concentrations to generate an intensity curve. To determine the quantity of enzyme in an unknown test sample, the signal intensity may then be converted to enzyme concentration according to the intensity curve. It should be understood that, as discussed above with respect to the first detection zone 31, so long as one distinct region of the second detection zone 35 satisfies the direct relationship, the signal intensity exhibited by the second detection zone 35 is considered directly proportional to the enzyme concentration.

Also, an inverse relationship may exist between the signal intensity at the first detection zone 31 ($I_1$) and the second detection zone 35 ($I_2$). For example, because a predetermined amount of reporters are present, the amount captured at the second detection zone 35 is inversely proportional to the amount captured at the first detection zone 31. As a result of this inverse relationship, the concentration of the enzyme may, in some cases, be more effectively measured over an extended range by comparing the signal intensity at both detection zones. For example, in one embodiment, the amount of enzyme is directly proportional to the ratio of the signal intensity "$I_2$" to the signal intensity "$I_1$." Based upon the range in which this ratio falls, the general concentration range for the enzyme may be determined. If desired, the ratio of $I_2$ to $I_1$ may be plotted versus enzyme concentration for a range of known enzyme concentrations to generate an intensity curve. To determine the quantity of enzyme in an unknown test sample, the signal intensity ratio may then be converted to enzyme concentration according to the intensity curve. It should be noted that alternative mathematical relationships between $I_1$ and $I_2$ may be plotted versus the enzyme concentration to generate the intensity curve. For example, in one embodiment, the value of $I_2/(I_2+I_1)$ may be plotted versus enzyme concentration to generate the intensity curve.

As stated above, certain embodiments of the present invention may utilize a reporter that is not directly detectable. Thus, when released, it is generally desired that the reporter interact in some manner with a detectable substance for subsequent detection. For example, probes capable of generating a detectable signal may be employed that are configured to bind to the released reporters. For example, probes may contain particles labeled or otherwise applied with the detectable substance. In some instances, it is desired to modify the probes in some manner. For example, the probes may be modified with a specific binding member to form conjugated probes that have specific affinity for the released reporters. The specific binding members may generally be conjugated to the probes using any of a variety of well-known techniques, such as through covalent bonding and/or physical adsorption in a manner such as described above. In one particular embodiment, carboxylic groups on the probe surface are activated and reacted with amino groups of the specific binding member to form an amide bond. When utilized, it is generally desired that the specific binding pair used for the probes and reporter is different than the specific binding pair used for the first receptive material and the other specific binding member joined to the substrate. This helps to ensure that the probes and reporters do not substantially interfere with the binding mechanism described above.

The probes may be contacted with the released reporters at any stage of the enzyme detection process. For example, in some embodiments, the probes may be applied to the assay device 20 at a location upstream from the region in which detection is desired. For example, in one embodiment, the probes may be applied to a conjugated pad (not shown) that is located upstream from the detection zone 31 and 35, but downstream from the sample pad 22.

In such embodiments, a variety of assay formats may be used to detect the released reporters. In one embodiment, for example, a "sandwich" assay format is utilized in which the released reporter is selected to have an affinity for the specific binding member of the conjugated probe. The released reporter, such as antibodies, antigens, etc., typically has two or more binding sites (e.g., epitopes). One of these binding sites becomes occupied by the specific binding member of the conjugated probe. However, the free binding site of the released reporter may subsequently bind to a receptive material immobilized within the second detection zone 35 to form a new ternary sandwich complex. Alternatively, the released reporter may be detected using direct or indirect "competitive" assay formats. In such instances, the specific binding member of the conjugated probe may be the same as or an analog of the released reporter. Thus, upon reaching the second detection zone 35, the conjugated detection probes and the released reporters compete for available binding sites of the immobilized receptive material. Of course, any other assay format is also suitable for use in the present invention.

For the embodiments described above in which the reporters are indirectly detectable, an increase in enzyme concentration within the test sample results in the release in a greater number of reporters. Thus, if a sandwich assay format is used, more released reporters bind to the conjugated probes so that the amount of enzyme is directly proportional to the signal intensity at the second detection zone 35. On the other hand, if a competitive assay format is used, the amount of enzyme is inversely proportional to the signal intensity at the second detection zone 35. In any event, the signal intensity may be plotted versus the enzyme concentration for a range of known enzyme concentrations to generate an intensity curve. To determine the quantity of enzyme in an unknown test sample, the signal intensity may then be converted to enzyme concentration according to the intensity curve.

Figure 3:
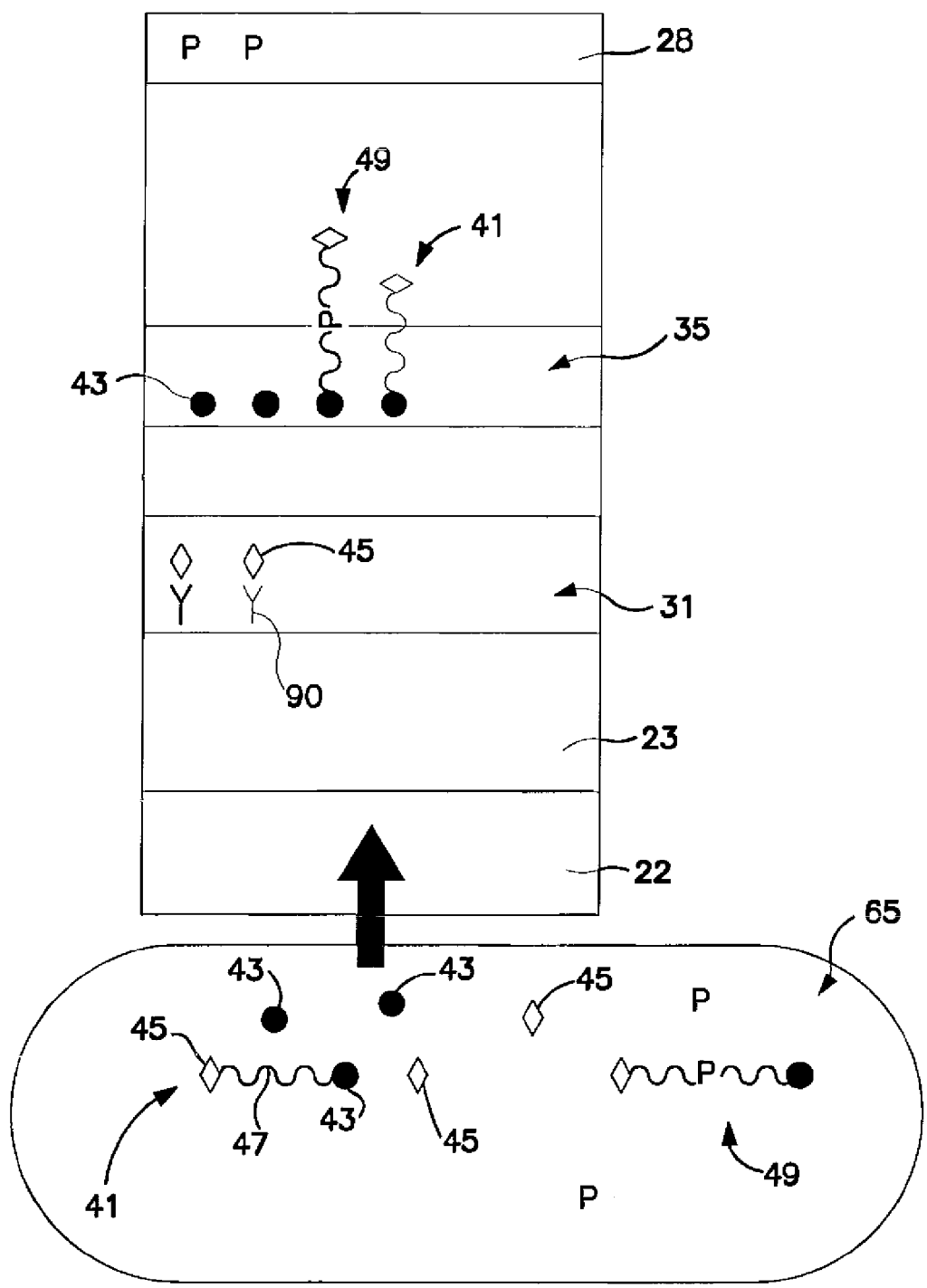
FIG. 3 is a schematic illustration of one assaying technique that may be used in one embodiment of the present invention to detect the presence or quantity of an enzyme within a test sample.

Referring to FIG. 3, one particular embodiment of a method for detecting the presence of a protease using fluorescence will now be described in more detail. Initially, a test sample containing a protease P is mixed with reactive complexes 41 that each include a fluorescent particle 43 and specific binding member 45 (e.g., biotinylated substance) joined to a substrate 47 (e.g., protein or glycoprotein). The complexes 41 are allowed to incubate for a sufficient period of time to form an incubation mixture (designated numeral 65 in FIG. 3) that includes released fluorescent particles 43 and specific binding members 45, as well as an unreacted complex 41, partially cleaved complex 49, protease P, and any product (not shown) generated by the enzyme-catalyzed reaction. The incubation mixture 65 is applied to the sample pad 22, as indicated by the illustrated directional arrow, and then travels to the first detection zone 31. Due to their smaller size, the released specific binding members 45 flow faster and have a higher probability of being captured by a first receptive material 90 within the first detection zone 31. The available binding sites in the first detection zone 31 may also be occupied by some of the unreacted complexes 41 and partially cleaved complexes 49. However, any unreacted complexes 41 and partially cleaved complexes 49 not captured by the first detection zone 31 travel to a second detection zone 35 and bind to a second receptive material (not shown) contained therein. Because the released fluorescent particles 43 do not have an affinity for the first receptive material 90, they also travel to the second detection zone 35 and bind to the second receptive material.

Once captured, the signal intensity of the fluorescent particles 43 may be measured at the first detection zone 31 and/or the second detection zone 35. Fluorescence detection generally utilizes wavelength filtering to isolate the emission photons from the excitation photons, and a detector that registers emission photons and produces a recordable output, usually as an electrical signal or a photographic image. One suitable fluorescence detector for use with the present invention is a FluoroLog III Spectrofluorometer, which is sold by SPEX Industries, Inc. of Edison, N.J. Another example of a suitable fluorescence detector is described in U.S. Patent Application Publication No. 2004/0043502 to Song, et al., which is incorporated herein in its entirety by reference thereto for all purposes. Although the use of fluorescence is utilized in this particular embodiment, it should be understood that any other known detection technique may also be utilized in the present invention. For example, other suitable optical detection techniques may include, but not limited to, phosphorescence, diffraction, reflectance, transmittance, etc. The optical reader may be capable of emitting light and also registering a detection signal (e.g., transmitted or reflected light, emitted fluorescence or phosphorescence, etc.). For example, in one embodiment, a reflectance spectrophotometer or reader may be utilized to detect the presence of reporters that exhibit a visual color (e.g. dyed latex microparticles). One suitable reflectance reader is described, for instance, in U.S. Patent App. Pub. No. 2003/0119202 to Kaylor, et al., which is incorporated herein in its entirety by reference thereto for all purposes.

Regardless of the technique used to measure signal intensity, the absolute amount of the protease P may be ascertained by comparing the signal intensity at the first detection zone 31 with the signal intensity at the second detection zone 35. For example, as indicated above, the amount of the protease P may be determined by the ratio $I_2/I_1$, and converting this ratio to an enzyme concentration using a previously ascertained intensity curve. Alternatively, the signal intensities $I_1$ or $I_2$ may also be used independently to indicate the presence or concentration of the enzyme. Of course, the present invention also contemplates qualitative embodiments in which the mere presence of the enzyme is confirmed by a signal intensity without a particular correlation to an actual enzyme concentration.

The aforementioned detection techniques are described specifically in the context of enzymes. However, as stated, the present invention is equally suitable for detecting the presence or quantity of an enzyme inhibitor within a test sample. To detect the presence of an enzyme inhibitor within a test sample, a predetermined quantity of a corresponding enzyme may be mixed with the test sample and allowed to incubate. In the presence of a certain amount of an enzyme inhibitor, the enzyme-catalyzed reaction does not proceed at a detectable rate. Thus, the relationship between enzyme inhibitor concentration and signal intensity will be opposite to the relationship between enzyme concentration and signal intensity. As an illustration, an enzyme-catalyzed reaction will not occur in the presence of a certain amount of inhibitor. Thus, all of the reactive complexes will be captured at the detection zone 31, which generates its maximum signal intensity. On the other hand, as the amount of enzyme inhibitor is reduced, the enzyme causes the reporters to release from the reactive complexes as described above. The signal intensity generated at the detection zone 31 thus begins to decrease due to a corresponding decrease in the presence of released reporters. Likewise, the signal intensity generated at the detection zone 35 may, in some embodiments, begin to increase due to a corresponding increase in the presence of released reporters. Accordingly, in this particular embodiment, the amount of enzyme inhibitor within the test sample is inversely proportional to the signal intensity at the detection zone 31 and directly proportional to the signal intensity at the detection zone 35.

It has been discovered that the diagnostic test kit of the present invention provides a relatively simple and cost-efficient method to quickly perform on-site testing of enzymes or their inhibitors. The test kit may provide a test result that is visible so that it is easily observed by the person performing the test in a prompt manner and under test conditions conducive to highly reliable and consistent test results. The diagnostic test kit is also disposable so that, if desired, it may be discarded when the test is concluded.

The present invention may be better understood with reference to the following examples.

EXAMPLE 1

β-casein was initially conjugated to fluorescent particles. Specifically, 2 milliliters of red carboxylated FluoroSphere particles (0.5-micrometer particle size, 2% solids content, Molecular Probes, Inc. of Eugene Oreg.) were washed once with phosphate-buffered saline (PBS) (Polysciences, Inc. of Warrington, Pa.) and then suspended in 1 milliliter of PBS. 36 milligrams of carbodiimide (Polysciences, Inc.) in 1 milliliter of PBS were added and the resulting mixture was shaken for 30 minutes. The particles were washed twice with a borate buffer (Polysciences, Inc.), and then suspended in 1 milliliter of borate buffer. 1 milligram of β-casein (Sigma-Aldrich Chemical Co., Inc. of St. Louis, Mo.) was added and the mixture was shaken overnight at room temperature. The particles were washed once with the borate buffer and then re-suspended in 500 microliters of borate buffer. 1 milliliter of ethanolamine solution (0.1 molar, Polysciences Inc.) was added to the particles and shaken for 30 minutes. The particles were then washed four times with water and suspended in 2 milliliters of borate buffer.

Upon formation, the conjugated particles (hereinafter "FCM-casein") were then biotinylated. Specifically, 4 milligrams of the FCM-casein particles in 200 microliters of borate buffer were mixed with 1 milligram of EZ-Link® Sulfo-NHS-LC-Biotin (Pierce Biotechnology, Inc. of Rockford, Ill.) in 200 microliters of borate buffer. The mixture was shaken overnight and then washed five times with water. The washed particles were suspended in 1 milliliter of tris buffer (pH of 7.2, 20 millimolar). The biotinylated conjugated particles are hereinafter referred to as "FCM-casein-B."

EXAMPLE 2

β-casein was initially conjugated to dyed particles. Specifically, 2 milliliters of blue carboxylated particles (0.3-micrometer particle size, Bangs Laboratories, Inc. of Fisher, Ind.) were washed once with phosphate-buffered saline (PBS from Polysciences, Inc. of Warrington, Pa.) and then suspended in 1 milliliter of PBS. 36 milligrams of carbodiimide (Polysciences, Inc.) in 1 milliliter of PBS were added and the mixture was shaken for 30 minutes. The particles were washed twice with a borate buffer (Polysciences, Inc.), and then suspended in 1 milliliter of borate buffer. 1 milligram of β-casein (Sigma-Aldrich Chemical Co., Inc. of St. Louis, Mo.) was added and the mixture was shaken overnight at room temperature. The particles were washed once with the borate buffer and then re-suspended in 500 microliters of borate buffer. 1 milliliter of ethanolamine solution (0.1 molar, Polysciences Inc.) was added to the particles and shaken for 30 minutes. The particles were then washed four times with water and suspended in 2 milliliters of borate buffer.

Upon formation, the conjugated particles (hereinafter "BP-casein") were then biotinylated. Specifically, 4 milligrams of the BP-casein particles in 200 microliters of borate buffer were mixed with 1 milligram of EZ-Link® Sulfo-NHS-LC-Biotin (Pierce Biotechnology, Inc. of Rockford, Ill.) in 200 microliters of borate buffer. The mixture was shaken overnight and then washed five times with water. The washed particles were suspended in 1 milliliter of tris buffer (pH of 7.2, 20 millimolar). The biotinylated conjugated particles are hereinafter referred to as "BP-casein-B."

EXAMPLE 3

The ability to detect the presence or absence of an enzyme in accordance with the present invention was demonstrated. Initially, one end of a nitrocellulose porous membrane (HF 12002 from Millipore, Inc. of Bedford, Mass.) was laminated with a cellulosic wicking pad (Millipore, Inc.). Streptavidin (1 milligram per milliliter, Sigma-Aldrich Chemical Co., Inc.) was striped onto the membrane to form a first detection zone. The laminated card was dried at 37° C. for 1 hour, and then cut into 4-millimeter wide assay devices.

25 microliters of the "FCM-casein-B" formed in Example 1 (4 milligrams per milliliter) and 75 microliters of tris buffer (pH of 7.4) were added to each of two wells (one sample well and one control well) present on a microtiter plate. 5 microliters of an active protease from *Bacillus polymyxa* (20 milligrams/milliliter), a metalloenzyme available from Sigma-Aldrich Chemical Co., Inc., were added to the sample well. Further, 5 microliters of a deactivated protease were added to the control well. The deactivated protease was obtained by boiling the active protease for 5 minutes. The mixtures in each well were allowed to react for 20 minutes. 20 microliters of each mixture was then transferred to a well containing 20 microliters of Tween 20 (2%, Sigma-Aldrich Chemical Co., Inc.).

The assay device samples were then inserted into each respective well to initiate the test. After allowing the assay to develop for 10 minutes, the color intensity of each detection zone was observed. Specifically, a red line was observed on the detection zone of the assay device inserted into the control well, while no red line was observed on the assay device inserted into the sample well. Thus, the signal intensity exhibited by the detection zone decreased in the presence of the enzyme.

EXAMPLE 4

The ability to detect the presence or absence of an enzyme in accordance with the present invention was demonstrated. Initially, one end of a nitrocellulose porous membrane (HF 12002, Millipore, Inc.) was laminated with a cellulosic wicking pad (Millipore, Inc.). Streptavidin (1 milligram per milliliter, Sigma-Aldrich Chemical Co., Inc.) was striped onto the membrane to form a first detection zone. A second detection zone was also formed by striping the membrane with Goldline™ (a polylysine solution available from British Biocell International). The laminated card was dried at 37° C. for 1 hour, and then cut into 4-millimeter wide assay devices.

Six samples (designated as Samples 1-6) were then provided that contained 25 microliters of the "FCM-casein-B" formed in Example 1 (4 milligrams/milliliter). Each sample was incubated for 15 minutes with different amounts of an active protease from *Bacillus polymyxa* (20 milligrams/milliliter), a metalloenzyme available from Sigma-Aldrich Chemical Co., Inc. Specifically, the amount of active protease in Samples 1-6 ranged from 0.0, 0.2, 1.0, 2.0, 10.0, and 20.0 micrograms, respectively. For Sample 1 (control sample), 20 micrograms of deactivated protease (obtained by boiling for 30 minutes) was also added. After incubation, 2 microliters of each mixture was then transferred to a well containing 40 microliters of Tween 20 (1%, Sigma-Aldrich Chemical Co., Inc.).

The assay device samples were then inserted into each respective well to initiate the test. After allowing the assay to develop for 10 minutes, the color intensity of each detection zone was observed. The qualitative results are set forth below in Table 1.

TABLE 1

Qualitative Color Intensity for Detection Zones

| Sample | First Detection Zone | Second Detection Zone |
|---|---|---|
| 1 | Strong | None |
| 2 | Medium | Weak |
| 3 | Medium | Strong |
| 4 | Weak | Strong |
| 5 | None | Strong |
| 6 | None | Strong |

As indicated, the signal intensity exhibited by the first detection zone decreased in the presence of the enzyme, while the signal intensity exhibited by the second detection zone increased in the presence of the enzyme.

EXAMPLE 5

The ability to detect the presence or absence of an enzyme in accordance with the present invention was demonstrated. Initially, one end of a nitrocellulose porous membrane (HF 12002, Millipore, Inc.) was laminated with a cellulosic wicking pad (Millipore, Inc.). Streptavidin (1 milligram per milliliter, Sigma-Aldrich Chemical Co., Inc.) was striped onto the membrane to form a first detection zone. A second detection zone was also formed by striping the membrane with Goldline™ (a polylysine solution available from British Biocell International). The laminated card was dried at 37° C. for 1 hour, and then cut into 4-millimeter wide assay devices.

Six samples (designated as Samples 1-6) were then provided that contained 50 micrograms of the "BP-casein-B" formed in Example 2. Each sample was incubated for 10 minutes with different amounts of an active protease from *Bacillus polymyxa* (20 milligrams/milliliter), a metalloenzyme available from Sigma-Aldrich Chemical Co., Inc. Specifically, the amount of active protease in Samples 1-6 ranged from 0, 5, 10, 20, 40, 200 nanograms, respectively. For Sample 1 (control sample), 20 micrograms of deactivated protease (obtained by boiling for 30 minutes) was also added. After incubation, 2 microliters of each mixture was then transferred to a well containing 40 microliters of Tween 20 (1%, Sigma-Aldrich Chemical Co., Inc.).

The assay device samples were then inserted into each respective well to initiate the test. After allowing the assay to develop for 10 minutes, the reflectance intensity of each detection zone was measured using a reflectance reader. The quantitative results are set forth below in Table 2.

TABLE 2

Quantitative Color Intensity for Detection Zones

| Sample | Reflectance Intensity ($I_1$) of First Detection Zone | Reflectance Intensity ($I_2$) of Second Detection Zone | Ratio of $I_2/I_1$ |
|---|---|---|---|
| 1 | 2.061 | 0.023 | 0.011 |
| 2 | 1.449 | 0.832 | 0.574 |
| 3 | 1.357 | 1.090 | 0.803 |
| 4 | 1.402 | 1.399 | 0.998 |
| 5 | 1.004 | 1.469 | 1.463 |
| 6 | 0.538 | 0.992 | 1.844 |

As indicated, the signal intensity exhibited by the first detection zone decreased in the presence of the enzyme, while the signal intensity exhibited by the second detection zone increased in the presence of the enzyme. Also, the ratio, $I_2/I_1$, increased in the presence of the enzyme.

EXAMPLE 6

The ability to detect the presence or absence of an enzyme in accordance with the present invention was demonstrated. Initially, one end of a nitrocellulose porous membrane (HF 12002, Millipore, Inc.) was laminated with a cellulosic wicking pad (Millipore, Inc.). Two distinct lines of streptavidin (1 milligram per milliliter, Sigma-Aldrich Chemical Co., Inc.) were striped onto the membrane to form a first detection zone. A second detection zone was also formed by striping the membrane with Goldline™ (a polylysine solution available from British Biocell International). The laminated card was dried at 37° C. for 1 hour, and then cut into 4-millimeter wide assay devices.

Six samples (designated as Samples 1-6) were then provided that contained 5 microliters of the "FCM-casein-B" formed in Example 1 (4 milligrams/milliliter). Each sample was incubated for 10 minutes with different amounts of an active protease from Bacillus polymyxa (20 milligrams/milliliter), a metalloenzyme available from Sigma-Aldrich Chemical Co., Inc. Specifically, the amount of active protease in Samples 1-6 ranged from 0.0, 0.1, 0.2, 1.0, 2.0, and 10.0 micrograms, respectively. For Sample 1 (control sample), 20 micrograms of deactivated protease (obtained by boiling for 30 minutes) was also added. After incubation, 2 microliters of each mixture was then transferred to a well containing 40 microliters of Tween 20 (1%, Sigma-Aldrich Chemical Co., Inc.).

The assay device samples were then inserted into each respective well to initiate the test. After allowing the assay to develop for 10 minutes, the color intensity of each detection zone was observed. The qualitative results are set forth below in Table 3.

TABLE 3

Qualitative Color Intensity for Detection Zones

| Sample | First Detection Zone (First Line) | First Detection Zone (Second Line, downstream from First Line) | Second Detection Zone |
|---|---|---|---|
| 1 | Strong | Weak | None |
| 2 | Strong | Medium | None |
| 3 | Medium | Medium | Medium |
| 4 | Medium | Medium | Medium |
| 5 | Weak | Weak | Strong |
| 6 | None | None | Strong |

As indicated, the signal intensity exhibited by the first line of the first detection zone decreased in the presence of the enzyme, while the signal intensity exhibited by the second detection zone increased in the presence of the enzyme. The signal intensity exhibited by the second line of the first detection zone initially increased, but then decreased in the presence of the enzyme.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diagnostic kit for detecting an enzyme, or an inhibitor thereof, within a test sample, the kit comprising:
a plurality of reactive complexes that each comprises a substrate joined to a reporter and specific binding member, said substrate being cleavable by the enzyme; and
a chromatographic medium through which the test sample flows that defines a first detection zone within which a first receptive material is immobilized that has an affinity for said specific binding member, wherein the chromatographic medium further comprises a second detection zone within which a second receptive material is immobilized, the second receptive material having an affinity for the reporter or complexes thereof, the reporter being capable of directly or indirectly generating a first detection signal within the first detection zone and a second detection signal within the second detection zone.

2. A diagnostic test kit as defined in claim 1, wherein the enzyme is a hydrolase.

3. A diagnostic test kit as defined in claim 2, wherein the hydrolase is a protease or peptidase.

4. A diagnostic test kit as defined in claim 2, wherein the hydrolase is a serine protease, aspartic protease, thiol protease, metalloprotease, acid protease, or alkaline protease.

5. A diagnostic test kit as defined in claim 1, wherein said substrate is a protein, glycoprotein, peptide, nucleic acid, carbohydrate, lipid, or ester.

6. A diagnostic test kit as defined in claim 5, wherein said substrate is casein, albumin, hemoglobin, myoglobin, keratin, gelatin, insulin, proteoglycan, fibronectin, laminin, collagen, or elastin.

7. A diagnostic test kit as defined in claim 1, wherein said reporter comprises a detectable substance that is capable of directly generating said first detection signal.

8. A diagnostic test kit as defined in claim 1, wherein said reporter comprises a specific binding member.

9. A diagnostic test kit as defined in claim 8, further comprising probes conjugated with a specific binding member, said probes further comprising a detectable substance that is capable of directly generating said first detection signal.

10. A diagnostic test kit as defined in claim 9, wherein said specific binding member of said probes has specific binding affinity for said specific binding member of said reporter.

11. A diagnostic test kit as defined in claim 9, wherein said specific binding member of said probes is the same as said specific binding member of said reporter.

12. A diagnostic test kit as defined in claim 1, wherein said specific binding member is selected from the group consisting of antibodies, antigens, haptens, biotin, avidin, streptavidin, neutravidin, captavidin, protein A, protein G, carbohydrates, lectins, nucleotide sequences, peptide sequences, effector and receptor molecules, hormone and hormone binding protein, enzyme cofactors, enzymes, and enzyme inhibitors.

13. A diagnostic test kit as defined in claim 1, wherein the total quantity of said first receptive material is less than otherwise needed to bind to the total quantity of said reactive complexes.

14. A diagnostic test kit as defined in claim 1, wherein the total quantity of said first receptive material is the same or more than otherwise needed to bind to the total quantity of said reactive complexes.

15. A diagnostic test kit as defined in claim 1, wherein said second receptive material is a specific binding member.

16. A diagnostic test kit as defined in claim 1, wherein said second receptive material comprises a polyelectrolyte.

17. A diagnostic test kit as defined in claim 1, wherein the amount of an enzyme within the test sample is directly proportional to the intensity of said second detection signal.

18. A diagnostic test kit as defined in claim 1, wherein the amount of an enzyme within the test sample is directly proportional to the ratio of the intensity of said second detection signal to the intensity of said first detection signal.

19. A diagnostic test kit as defined in claim 1, wherein the amount of an enzyme within the test sample is inversely proportional to the intensity of said first detection signal.

20. A diagnostic test kit as defined in claim 1, wherein the amount of an enzyme inhibitor within the test sample is directly proportional to the intensity of said first detection signal.

* * * * *